United States Patent [19]

Arndt

[11] Patent Number: 5,599,992
[45] Date of Patent: Feb. 4, 1997

[54] PROCESS FOR THE PREPARATION OF 2-FLUOROPHENYLHYDRAZINE

[75] Inventor: Otto Arndt, Hofheim, Germany

[73] Assignee: Hoechst Aktiengesellschaft, Germany

[21] Appl. No.: 589,859

[22] Filed: Jan. 22, 1996

[30]   Foreign Application Priority Data

Jan. 24, 1995 [DE] Germany ............... 195 01 948.2

[51] Int. Cl.$^6$ .................................. C07C 241/02
[52] U.S. Cl. ........................................... 564/314
[58] Field of Search .............................. 564/314

[56] References Cited

U.S. PATENT DOCUMENTS 3,410,900  11/1968  Kindler et al. .................. 260/569

FOREIGN PATENT DOCUMENTS 1180375  10/1964  Germany .
 220841   4/1985  Germany .
 475203   7/1969  Switzerland .

OTHER PUBLICATIONS

Patent Abstracts of Japan, vol. 11, No. 80, Mar. 11, 1987; JP-A-61 233656 (Nippon Nohyaku Co Ltd), Oct. 17, 1986.
Patent Abstracts of Japan, vol. 5, No. 67, May 7, 1981; JP-A-56 016454 (Mitsubishi Kasei Kogyo K.K.), Feb. 17, 1981.

*Primary Examiner*—Peter O'Sullivan
*Attorney, Agent, or Firm*—Connolly and Hutz

[57] ABSTRACT

The invention relates to a process for the preparation of 2-fluorophenylhydrazine or 2-fluorophenylhydrazine hydrochloride, which comprises diazotizing 2-fluoroaniline, reducing the resulting diazonium salt with alkaline bisulfite solution to give 2-fluorophenylhydrazine $\alpha\beta$-disulfonate, hydrolyzing the latter with hydrochloric acid to give 2-fluorophenylhydrazine hydrochloride, adding alkali metal solution to neutralize the mixture, subsequently cooling the mixture, removing the 2-fluorophenylhydrazine precipitate by filtration and, if appropriate, reacting the latter with hydrochloric acid to give 2-fluorophenylhydrazine hydrochloride.

19 Claims, No Drawings

PROCESS FOR THE PREPARATION OF 2-FLUOROPHENYLHYDRAZINE

DESCRIPTION

The invention relates to a process for the preparation of 2-fluorophenylhydrazine.

2-Fluorophenylhydrazine is a valuable intermediate for the preparation of crop protection agents.

The preparation of halogenated phenyl hydrazines is described in the literature.

Methoden der Org. Chemie [Methods in Organic Chemistry](Houben-Weyl), 4th Ed., Vol. X/2 (1967), p. 178 et seq. recommends the hydrazinolysis of halogen compounds to prepare this class of compounds. However, the same publication also describes the preparation of 2-chlorophenylhydrazine hydrochloride by means of reduction using sodium sulfite. In this case, however, a yield of only 50% is obtained.

Several other references also confirm that the preparation of halophenylhydrazines by means of reduction of the corresponding diazoniumsalts using hydrogen sulfite does not lead to satisfactory results: Ber. 66, 727 (1933) describes the preparation of 4-fluorophenylhydrazine by means of reduction using sodium sulfite/zinc dust, the yield being approximately 75%.

J. Chem. Soc. 1953, p. 3326 and J. Chem. Soc. 1945, p. 530 make reference to the poor results obtained when the reduction is carried out using sulfite and recommend to carry out the reduction using tin chloride in a large excess of hydrochloric acid.

This method results in high pollution of the waste water, but only moderate yields.

Acta Chimika Hungary 7 (1955) p. 65–68 describes the reduction of the diazo compounds with $SO_2$ as the best method for the preparation of fluorophenylhydrazines. This procedure has several severe disadvantages: the use of sulfuric acid in place of hydrochloric acid in the diazotization requires the use of approximately 80% more acid. The reduction step described is characterized by a very poor space yield (10 l of water per mole of fluoroaniline), large amounts of $SO_2$ in the waste gas and high energy requirements.

Moreover, most of the methods described have the disadvantage that liberation of the hydrazine base from the hydrochloride does not take place in the reaction mixture but the hydrochloride is first isolated and the hydrazine is subsequently liberated using sodium hydroxide solution and an additional solvent as extractants.

There was therefore a demand for a process which allows 2-fluorophenylhydrazine to be prepared in high yield combined with low pollution of the waste water.

This object is achieved by a process for the preparation of 2-fluorophenylhydrazine or 2-fluorophenylhydrazine hydrochloride which comprises diazotizing 2-fluoroaniline, reducing the diazonium salt obtained with alkaline bisulfite solution to give 2-fluorophenylhydrazine α,β-disulfonate, hydrolyzing the latter with hydrochloric acid to give 2-fluorophenylhydrazine hydrochloride, adding alkali metal solution to neutralize the reaction mixture, subsequently cooling the mixture, removing the 2-fluorophenylhydrazine precipitate by filtration and, if appropriate, reacting the product with hydrochloric acid to give 2-fluorophenylhydrazine hydrochloride.

The alkaline bisulfite solution employed is advantageously a mixture of alkali metal hydrogen sulfite and alkali metal hydroxide, the sodium and potassium salts being particularly suitable. This mixture can be employed both as an aqueous solution and as a solid. It has proved advantageous to reduce the diazonium salt at a pH of 4.5 to 7.5, in particular 5.6 to 6.5, using $NaHSO_3$/NaOH and to neutralize 2-fluorophenylhydrazine hydrochloride at temperatures from 0° to 100° C., in particular 15° to 60° C. To isolate the product, it is advantageous to cool the batch to 5° to 50° C., in particular 15° to 30° C. The resulting product can be dehydrated in vacuo in the melt.

The process can be carried out particularly advantageously by diazotizing 2-fluoroaniline with nitrose acid in the presence of a defined excess of hydrochloric acid (3.0 to 3.5, in particular 3.2, moles of HCl per mole of 2-fluoroaniline), subsequently reducing the diazonium salt with sodium hydrogen sulfite/NaOH (2.2 mol of NaOH, 2.2 mol of $NaHSO_3$ per mole of 2-fluoroaniline) in a certain pH range (pH=5.7 to 6.5) to give 2-fluorophenylhydrazine α,β-disulfonate, then hydrolyzing the disulfonate at high temperatures and in the presence of hydrochloric acid to give 2-fluorophenylhydrazine hydrochloride, running in the concentrated sodium hydroxide solution to neutralize the 2-fluorophenylhydrazine hydrochloride reaction mixture, allowing the temperature during running of the concentrated sodium hydroxide solution onto the reaction mixture to climb to eventually approximately 60° C. by means of the heat of neutralization to such an extent that, in the course of the temperature gradient, a temperature is reached even before the first quantities of the free hydrazine base start to precipitate (from pH 3.5 to 4.0) which is above the melting point of the free hydrazine base of approximately 45° to 50° C. in the presence of the reaction mixture. Accordingly, the proportion of solid free hydrazine base formed in the reaction mixture is low. Finally, a liquid two-phase mixture of the aqueous mother liquor and an oily phase of the free hydrazine base is present. After a pH of 8 to 9 has been reached at 50° to 60° C., it has proved advantageous subsequently to cool the mixture to 18° to 22° C. to isolate the free hydrazine base. Cooling is advantageously effected slowly by means of gentle external cooling to avoid the crystallization of sodium sulfate dekahydrate, which may take place when the mixture is undercooled.

Surprisingly, the product, which crystallizes out starting at approximately 40° C., is coarsely particulate and granule-like. From this results a high dry-matter content and low content of inorganic salts. The necessity of phase separation above the-melting point to remove the alkaline salt solution which has separated out can be dispensed with.

The interesting aspect of the process according to the invention is that 2-fluorophenylhydrazine hydrochloride can be neutralized to the free 2-fluorophenylhydrazine even at elevated temperature. There was a prejudice in the literature against this procedure since for example Methoden der Organischen Chemie [Methods in Organic Chemistry], Houben-Weyl, Vol. X/2 (1967), p. 178 taught that mixtures of phenylhydrazine and phenylhydrazine hydrochloride show thermal decomposition even at below 100° C.

Surprisingly, it was possible to prepare 2-fluorophenylhydrazine by means of diazotization and bisulfite reduction, even though there was a prejudice against this preparation method (J. Chem. Soc. 1953, 3326 and J. Chem. Soc. 1945, 530).

The procedure according to the invention provides an advantageous possibility for the preparation of 2-fluorophenylhydrazine hydrochloride: the free hydrazine base is difficult to handle since filling and emptying of the containers can only be carried out when the substance is in the melt.

The hydrochloride, which is obtained in the form of a powder, can be handled more easily. The hydrochloride can be dried more readily, while residual water can only be removed from the free hydrazine base by technically complicated operations. It is therefore obvious to modify the preparation process starting from 2-fluoroaniline in such a way that the hydrochloride, which is formed as an intermediate, is isolated by filtration. However, it emerged that this procedure starting from 2-fluoroaniline has disadvantages. The higher solubility of the hydrochloride in the reaction mixture in comparison with the free hydrazine base necessitates more hydrochloric acid for the precipitation. Even then, there is still a marked yield loss. This results in greater pollution of the waste water with organic and inorganic material. Moreover, the crystalline hydrochloride isolated contains 5 to 10% of sodium sulfate.

The abovementioned yield loss can be compensated for by neutralizing the hydrochloric-acid-containing mother liquor of the hydrochloride using sodium hydroxide solution and then extracting the product using xylene. This gives 2-fluorophenylhydrazine in an amount of approximately one third of the yield. This large amount must be added to the next batch. This measure involves a high outlay.

Surprisingly, the hydrochloride can now be prepared in high yield and with an improved quality in comparison with the crude base starting from the free hydrazine base, which has been obtained by the above-described route. A prerequisite is that the crude base is free of sodium sulfate. This prerequisite is fulfilled when the above-described conditions according to the invention are met. To this end, the crude base is reacted with hydrochloric acid, precipitation of the hydrochloride with hydrochloric acid is completed, and 2-fluorophenylhydrazine hydrochloride is filtered off.

The examples which follow are intended to illustrate the process according to the invention without imposing any limitation. Parts are by weight:

EXAMPLES

Example 1:

In the course of the experiment, the reaction mixture is constantly stirred and nitrogen is introduced onto the mixture.

a) Preparation of the crude base 113.5 parts of 2-fluoroaniline are introduced into a mixture of 400 parts of water and 310 parts of 37% hydrochloric acid. 174 parts of 40% aqueous sodium nitrite solution are run in at 20° C. After destroying the excess nitrite with amidosulfuric acid, the diazonium salt solution is passed at 10° to 15° C. into a mixture of 550 parts of approximately 40% sodium hydrogen sulfite and 108 parts of 50% sodium hydroxide. While the diazonium salt solution is passed in further, approximately 70 parts of 50% sodium hydroxide are added dropwise simultaneously to maintain the pH at 5.4 to 6.0. The mixture is heated to 70° C. 245 parts of 37% hydrochloric acid are passed into the solution, which is still at a temperature of 70° C., while heating it to 75° to 80° C. Stirring is continued for 30 minutes and the batch is cooled to 30° C., during which process the hydrochloride of the 2-fluorophenylhydrazine crystallizes out starting at approximately 55° C. A recycling proportion of approximately 7 parts of the preceding batch, obtained from the mother liquor of the crude base and the washing filtrate, is added. Approximately 360 parts of 50% sodium hydroxide solution are run in, and the temperature is simultaneously increased steadily (linear gradient) from 30 to approximately 60° C. Precipitation of the free hydrazine base as a solid starts first at pH 3.8 and 45° C., but the solids proportion does not increase since melting starts soon. Neutralization ends at pH 8.5 and approximately 60° C.

Most of the product is dissolved in the aqueous phase. The liquid two-phase mixture (2400 to 2450 parts) is cooled from 50° to 20° C. Starting at approximately 40° to 45° C., the 2-fluorophenylhydrazine crystallizes out in the form of coarse crystals (granules). The mixture is filtered, and the filtercake is washed using 200 parts of water. Filtration only takes approximately 5 minutes. This gives approximately 130 to 180 parts of crude base with a dry-matter content of 115 parts of 2-fluorophenylhydrazine, which corresponds to 91% of theory. The space yield is approximately 60 parts per 1000 parts by volume.

b) Preparation of the hydrochloride To prepare the hydrochloride, the crude base is molten in a heatable metering funnel at 55° to 60° C. If it still contains sodium sulfate, the latter separates out as the bottom phase and must be separated off. The melt of the crude base is run into 164 parts of 20% hydrochloric acid at 60° to 65° C. Then, 90 parts of 37% hydrochloric acid are subsequently run in slowly at 60° to 65° C. The mixture is slowly cooled to 10° C. It is filtered at 10° C. 145 parts of 2-fluorophenylhydrazine hydrochloride (89% of theory) are obtained with a melting point of 208° to 210° C. if the abovementioned recycling proportion has been added. The 2-fluorophenylhydrazine hydrochloride content is 99.0 to 99.8% (alkalimetric and argentometric titration). The product contains no inorganic salts.

Example 2:

The procedure is as in Example 1, but the 2-fluorophenylhydrazine hydrochloride is neutralized in its hydrochloric-acid-containing reaction mixture using sodium hydroxide solution at a constant temperature of 20° C. over a period of 2 hours. A very thick suspension forms starting at pH 3.8 or approximately 265 parts of 50% sodium hydroxide solution. Finally, at pH 8.5, or after approximately 360 parts of 50% sodium hydroxide solution, a thick, stirable suspension is obtained, which is filtered. The filtercake is washed with 200 parts of water. 281 parts of water-moist crystals are obtained. After melting to 55° to 60° C., 128.5 parts of bottom product phase are obtained (melting point after solidification=45° to 47° C). The top aqueous phase amounts to 148 parts. The pure product content of the crude base was determined by fractional distillation as 87.2%. The water content amounted to approximately 10%. The distillation residue amounted to 2.6%.

I claim:

1. A process for the preparation of 2-fluorophenylhydrazine or 2-fluorophenylhydrazine hydrochloride, which comprises diazotizing 2-fluoroaniline, reducing the resulting diazonium salt with alkaline bisulfite solution to give 2-fluorophenyhydrazine α,β-disulfonate, hydrolyzing the latter with hydrochloric acid to give 2-fluorophenylhydrazine hydrochloride, adding alkali metal solution to neutralize the mixture, subsequently cooling the mixture, removing the 2-fluorophenylhydrazine precipitate by filtration and, optionally reacting the latter with hydrochloric acid to give 2-fluorophenylhydrazine hydrochloride.

2. The process as claimed in claim 1, wherein the alkaline bisulfite solution employed is a mixture of alkali metal hydrogen sulfite/alkali metal hydroxide.

3. The process as claimed in claim 1, wherein the diazonium salt is reduced to the 2-fluorophenylhydrazine α,β-disulfonate at a pH of 4.5 to 7.5.

4. The process as claimed in claim 1, wherein NaOH is used as the alkali metal hydroxide solution.

5. The process as claimed in claim 1, wherein the alkali metal hydroxide solution is added at a temperature of from 0° to 100° C. to neutralize the solution.

6. The process as claimed in claim 1, wherein 2-fluorophenylhydrazine is filtered off at a temperature of from 5° to 50° C.

7. The process as claimed in claim 1, wherein the 2-fluoroaniline is diazotized using nitrose acid in the presence of 3 to 3.5 mol, of hydrochloric acid per mole of 2-fluoroaniline.

8. The process as claimed in claim 1 wherein the diazonium salt is reduced using 2.2 mol of sodium hydrogen sulfite and 2.2 mol of NaOH per mole of 2-fluoroaniline.

9. The process as claimed in claim 1, wherein a temperature of 45 to approximately 55° C. is set when a pH of 3.5 to 4.0 is reached when adding the sodium hydroxide solution to neutralize the hydrochloride.

10. The process as claimed in claim 1, wherein the mixture is cooled to 18° to 22° C. when a pH of 8 to 9 is reached.

11. The process as claimed in claim 1, wherein the free base is liberated from the hydrochloride in the reaction mixture.

12. The process as claimed in claim 1, wherein sodium sulfate is removed from the crude base by means of phase separation in the product melt at 55° to 60° C.

13. The process as claimed in claim 1 wherein the free base is reacted with hydrochloric acid, precipitation of the 2-fluorophenylhydrazine hydrochloride with hydrochloric acid is completed and the 2-fluorophenylhydrazine hydrochloride is filtered off.

14. The process as claimed in claim 1, wherein the alkaline bisulfite solution employed is a mixture of sodium hydrogen sulfite or potassium hydrogen sulfite and sodium hydroxide or potassium hydroxide.

15. The process as claimed in claim 1, wherein the alkaline bisulfite solution employed is a mixture of sodium hydrogen sulfite and sodium hydroxide.

16. The process as claimed in claim 1, wherein the diazonium salt is reduced to the 2-fluorophenylhydrazine $\alpha,\beta$-disulfonate at a pH of 5.6 to 6.5.

17. The process as claimed in claim 1, wherein the alkali metal hydroxide solution is added at a temperature of from 15° to 60° C. to neutralize the solution.

18. The process as claimed in claim 1, wherein 2-fluorophenylhydrazine is filtered off at a temperature from 15° to 30° C.

19. The process as claimed in claim 1, wherein the 2-fluoroaniline is diazotized using nitrose acid in the presence of 3.2 mol of hydrochloric acid per mole of 2-fluoroaniline.

\* \* \* \* \*